United States Patent [19]

Yellin et al.

[11] 4,338,448
[45] Jul. 6, 1982

[54] 3-CHLOROALKYL-5-GUANIDINO-1,2,4-OXADIAZOLES

[75] Inventors: Tobias O. Yellin, Wallingford, Pa.; Derrick M. Mant, Bramhall, England

[73] Assignees: Imperial Chemical Industries Limited, London, England; ICI Americas Inc., Wilmington, Del.

[21] Appl. No.: 174,495

[22] Filed: Aug. 1, 1980

Related U.S. Application Data

[63] Continuation of Ser. No. 36,361, May 7, 1979, Pat. No. 4,242,351.

[30] Foreign Application Priority Data

May 24, 1978 [GB] United Kingdom ............... 21738/78

[51] Int. Cl.³ ............................................ C07D 271/06
[52] U.S. Cl. ................................................... 548/133
[58] Field of Search ......................................... 548/133

[56] References Cited

PUBLICATIONS

Yarugi, et al, "Chem. Pharm. Bull.," vol. 21, No. 8, (1973), pp. 1641–1650.

Primary Examiner—Anton H. Sutto
Attorney, Agent, or Firm—David J. Levy; John M. Sheehan

[57] ABSTRACT

The invention relates to oxadiazole derivatives which are histamine H-2 antagonists and which inhibit the secretion of gastric acid, to methods for their manufacture and to pharmaceutical compositions containing them. The oxadiazole derivatives are of the formula:

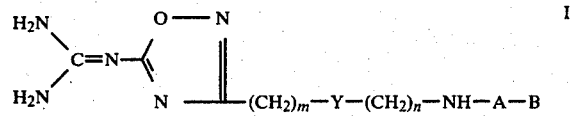

in which Y is O, S, $CH_2$ or a direct bond; m is 0 to 4 and n is 1 to 4, provided than when Y is S or O m is 1 to 4 and when Y is O n is 2 to 4; A is a 3,4-dioxocyclobuten-1,2-diyl radical or C=Z in which Z is O, S, NCN, $NNO_2$, $CHNO_2$, $NCONH_2$, $C(CN)_2$, $NCOR^1$, $NCO_2R^1$, $NSO_2R^1$ or $NR^2$ in which $R^1$ is alkyl or aryl and $R^2$ is H or alkyl; B is alkoxy or alkylthio or $NHR^3$ in which $R^3$ is H or alkyl; and the salts thereof.

2 Claims, No Drawings

3-CHLOROALKYL-5-GUANIDINO-1,2,4-OXADIAZOLES

This is a continuation, of application Ser. No. 36,361, filed May 7, 1979 now U.S. Pat. No. 4,242,351.

This invention relates to oxadiazole derivatives which are histamine H-2 antagonists and which inhibit gastric acid secretion.

It is postulated that the physiologically-active compound histamine, which occurs naturally within the animal body, is able to combine, in the course of exerting its activity, with certain specific receptors of which there are at least two distinct and separate types. The first has been named the H-1 receptor (Ash and Schild, *Brit. J. Pharmac.*, 1966, 27, 427) and the action of histamine at this receptor is blocked (antagonised) by classical "antihistamine" drugs such as mepyramine. The second histamine receptor has been named the H-2 receptor (Black et al., *Nature*, 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In UK Pat. Nos. 1,338,169 and 1,397,436 there are described histamine H-2 receptor antagonists which are heterocycles having a side chain to the end of which is attached, for example, an N-cyanoguanidine. It has now been discovered that if a guanidino radical is inserted in the 5-position of a 1,2,4-oxadiazole carrying such a side chain, there are produced compounds which are potent histamine H-2 receptor antagonists.

According to the invention there is provided an oxadiazole derivative of the formula I:

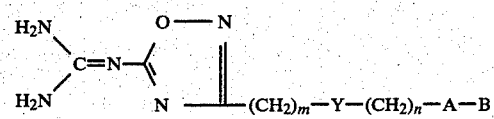

in which

Y is an oxygen or sulphur atom, a direct bond or a methylene radical; m is 0 to 4 and n is 1 to 4, provided that when Y is a sulphur or oxygen atom m is 1 to 4, and when Y is an oxygen atom n is 2 to 4;

A is a 3,4-dioxocyclobuten-1,2-diyl radical or a radical of the formula C=Z in which Z is an oxygen or sulphur atom or a radical of the formula NCN, NNO$_2$, CHNO$_2$, NCONH$_2$, C(CN)$_2$, or NCOR$^1$, NCO$_2$R$^1$, NSO$_2$R$^1$ or NR$^2$ in which R$^1$ is an alkyl radical of 1 to 6 carbon atoms or an aryl radical of 6 to 12 carbon atoms and R$^2$ is a hydrogen atom or an alkyl radical of 1 to 6 carbon atoms;

B is an alkoxy or alkylthio radical of 1 to 6 carbon atoms or a radical of the formula NHR$^3$ in which R$^3$ is a hydrogen atom or an alkyl radical of 1 to 10 carbon atoms;

and the pharmaceutically-acceptable acid-addition salts thereof.

It is to be understood that, in the above formula I and throughout this specification, although the double bonds in both side chains have been inserted in particular positions, various other tautomeric forms are possible, and this invention includes such tautomeric forms within its scope, both in terms of the compound of the invention, and in terms of the manufacturing processes.

A particular value for R$^1$ is a methyl or p-tolyl radical.

A particular value for R$^2$ is a methyl radical.

A particular value for B when it is an alkoxy or alkylthio radical is a methoxy, ethoxy or methylthio radical.

A particular value for R$^3$ when it is an alkyl radical is a methyl radical.

A preferred value for Y is a sulphur atom.

A preferred value for m is 1 and for n is 2.

A preferred value for A is a radical of the formula C=Z in which Z is a sulphur atom or a radical of the formula NCN or CHNO$_2$. A particularly preferred value for Z is a radical of the formula NCN or CHNO$_2$.

The following group of compounds is particularly preferred:

3-[2-(2-cyano-3-methylguanidino)ethylthiomethyl]-5-guanidino-1,2,4-oxadiazole.

3-[2-(2-cyanoguanidino)ethylthiomethyl]-5-guanidino-1,2,4-oxadiazole.

1-(2-[(5-guanidino-1,2,4-oxadiazol-3-yl)methylthio]ethyl)amino-1-methylamino-2-nitroethylene.

A suitable pharmaceutically-acceptable acid-addition salt of the oxadiazole derivative of the invention is, for example, a salt formed with hydrochloric, hydrobromic, phosphoric, sulphuric, acetic, citric or maleic acid.

The oxadiazole derivative of the invention may be manufactured by methods known in themselves for the manufacture of chemically-analogous compounds. Thus the following processes, Y, Z, m, n, A, B, R$^1$, R$^2$ and R$^3$ having the meaning stated above unless indicated otherwise, are provided as further features of the invention.

The process of the invention is characterised by:

(a) reaction of a compound of the formula II:

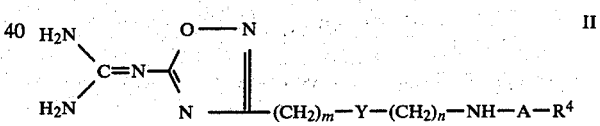

in which R$^4$ is a displaceable radical with a compound of the formula B-H;

(b) for those compounds in which A is a radical of the formula C=Z in which Z is a sulphur or oxygen atom and B is a radical of the formula NHR$^3$, reaction of a compound of the formula III:

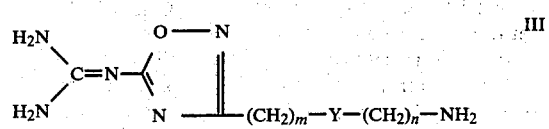

with a compound of the formula R$^3$—N=C=D in which D is an oxygen or sulphur atom;

(c) reaction of a compound of the formula III with a compound of the formula IV:

in which R$^4$ is a displaceable radical.

When the process of the invention manufactures the compound of the formula I in the form of the free base and an acid-addition salt is required, the compound of the formula I in the free base form is reacted with an acid which affords a pharmaceutically-acceptable anion.

Process (a) may be carried out using an excess of B-H, that is using an excess of the amine $R^3NH_2$, optionally in the presence of a diluent or solvent such as water, methanol, ethanol or pyridine, or using an excess of the alcohol $R^5OH$ or the thiol $R^5SH$ in which $R^5$ is an alkyl radical of 1 to 6 carbon atoms, preferably in the form of a salt such as the sodium salt in the same alcohol or thiol as diluent or solvent. $R^4$ may, for example, be an alkoxy or alkylthio radical of 1 to 6 carbon atoms, for example a methoxy, ethoxy or methylthio radical. The process may be accelerated or completed by the application of heat, for example by heating to the boiling point of the diluent or solvent.

Process (b) may be carried out using an excess of the isocyanate or isothiocyanate $R^3—N=C=D$. When D is a sulphur atom, the reaction is preferably carried out in a diluent or solvent such as methanol or ethanol. When D is an oxygen atom, a non-alcoholic diluent or solvent must be used.

Process (c) may be carried out using an excess of the compound of the formula IV in a diluent or solvent such as methanol, ethanol or acetonitrile. $R^4$ may, for example, be an alkoxy or alkylthio radical of 1 to 6 carbon atoms, for example a methoxy, ethoxy or methylthio radical. The reaction may be accelerated or completed by the application of heat, for example by heating to the boiling point of the diluent or solvent.

When Y is an oxygen or sulphur atom, the starting material of the formula III for use in process (b) or (c) may be prepared by reaction of a compound of the formula V:

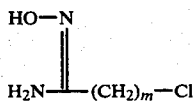   V with cyanoguanidine followed by reaction of the product, the compound of the formula VI:

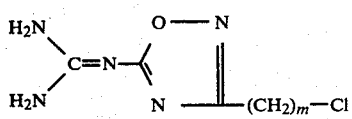   VI with a compound of the formula $HD-(CH_2)_n-NH_2$ in which D is an oxygen or sulphur atom, for example as set out in Example 1.

When Y is a direct bond or a methylene radical, the starting material of the formula III for use in process (b) or (c) may be prepared by reaction of a compound of the formula VII:

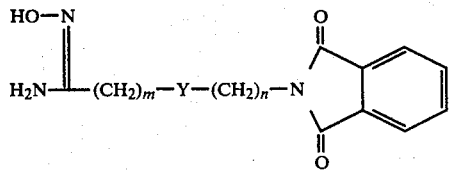   VII with cyanoguanidine followed by hydrolysis of the phthalimido residue in the product.

The starting material of the formula II for use in process (a) may be prepared by reaction of a compound of the formula III with a compound of the formula $R^4-A-R^4$ in which $R^4$ is a displaceable radical, for example an alkoxy or alkylthio radical, for example as set out in Example 1 or 5.

As noted above, the oxadiazole derivative of the invention is a histamine H-2 antagonist, inhibits the secretion of gastric acid in warm-blooded animals and is therefore useful in the treatment of peptic ulcers and other conditions caused or exacerbated by gastric acidity, including stress ulcers and gastro-intestinal bleeding due to trauma.

The histamine H-2 antagonist activity may be demonstrated on standard tests, for example by the ability of the compound of the formula I to inhibit the histamine-induced positive chronotropic response in the spontaneously beating right atrium of the guinea pig or by its ability to inhibit the histamine-induced increase in the level of cyclic AMP (in the presence of a phosphodiesterase inhibitor) in a free cell suspension obtained from canine gastric mucosa.

The guinea pig atrium test is carried out as follows:

A guinea pig right atrium is suspended at 1 g. tension (isometric) in thermostatically-controlled (30° C.) tissue bath (25 ml.) containing oxygenated (95% $O_2$; 5% $CO_2$) Krebs-Hanseleit buffer (pH 7.4). The tissue is allowed to stabilise over 1 hour during which time it is washed 2-4 times. Individual contractions are recorded with a force-displacement transducer through a strain gauge coupler, and instantaneous rates are monitored with a cardiotachometer. A control response to 1 $\mu M$ histamine is obtained after which the tissue is washed 3 times and allowed to re-equilibrate to basal rate. After re-equilibration for 15 minutes, the test compound is added to the desired final concentration. Ten minutes after addition of the compound histamine (1 $\mu M$) is again added and the response to histamine in the presence of antagonist is compared to the histamine control response. The result is expressed as a percentage of the histamine control response. Thereafter the apparent dissociation constant of the H-2 antagonist is determined by standard procedures.

All the compounds exemplified in this specification are active on the guinea pig atrium test at or below a bath concentration of 10 $\mu M$.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats, cats or dogs provided with gastric fistulae and whose gastric secretion is stimulated by the administration of a secretagogue, for example pentagastrin or histamine.

The test in dogs is carried out as follows:

A female pure bred beagle (9-12 kg.) having a chronic gastric fistula is fasted overnight with water ad lib. During the experiment the dog is lightly restrained in a standing position. When studying the test compound by the intravenous route, the fistula is opened and, after ascertaining the absence of basal secretion over a period of 30 minutes, a continuous intravenous infusion of secretagogue (0.5 $\mu$mole/kg/hour of histamine or 2 $\mu$g./kg./hour pentagastrin) in saline (15 ml./hour) is begun. Gastric acid samples are collected every 15 minutes. The volume of each sample is measured and a 1 ml. aliquot is titrated to neutrality with 0.1 NNaOH to determine acid concentration. When a plateau of secretion is reached (1-2 hours), the test compound is administered intravenously in saline and gastric acid samples are collected for a further 2-3 hours during which time the infusion of the secretagogue continues uninterrupted.

When studying the test compound by the intragastric route, the absence of basal secretion over a period of 30 minutes is ascertained and the test compound, contained in 25 ml. of 0.5% w/v hydroxypropyl methylcellulose and 0.1% w/v 'Tween' 80 in water ('Tween' is a Trade Mark), is instilled into the stomach through a fistula dosing plug. One hour later, the fistula is reopened and intravenous infusion of a secretagogue, as described above, is immediately begun. Gastric acid samples are measured as described above and the approach of acid secretion to a plateau is compared to that of a control animal which is dosed intragastrically only with the dosing vehicle.

When studying the test compound by the oral route, it is administered in a gelatin capsule washed down with 15 ml. of water. One hour later, the fistula is opened and intravenous infusion of the secretagogue is immediately begun. Gastric acid samples are measured as above and the approach of acid secretion to a plateau is compared to that of an undosed control animal.

The results obtained in the atrium test are predictive of activity in the dog test.

According to a further feature of the invention there is provided a pharmaceutical composition which comprises an oxadiazole derivative of the invention in association with a non-toxic pharmaceutically-acceptable diluent or carrier.

The pharmaceutical composition may, for example, be in a form suitable for oral, rectal, parenteral or topical administration, for which purposes it may be formulated by means known to the art into the form of, for example, tablets, capsules, aquous or oily solutions or suspensions, emulsions, dispersible powders, suppositories, sterile injectable aqueous or oily solutions or suspensions, gels, creams, ointments or lotions.

In addition to the oxadiazole derivative of the formula I, the pharmaceutical composition of the invention for oral, rectal or parenteral administration may also contain, or be co-adiminstered with, one or more known drugs selected from antacids, for example aluminium hydroxide—magnesium hydroxide mixtures; antipepsin compounds, for example pepstatin; other histamine H-2 antagonists, for example cimetidine; ulcer healing agents, for example carbenoxolone or bismuth salts; anti-inflammatory agents, for example ibuprofen, indomethacin, naproxen or aspirin; prostaglandins, for example 16,16-dimethylprostaglandin $E_2$; classical antihistamines (histamine H-1 antagonists), for example mepyramine or diphenhydramine; anticholinergic agents, for example atropine or propantheline bromide; anxiolytic agents, for example diazepam, chlordiazepoxide or phenobarbital.

The pharmaceutical composition of the invention for topical administration may also contain, in addition to the oxadiazole derivative, one or more classical antihistamines (histamine H-1 antagonists), for example mepyramine or diphenhydramine and/or one or more steroidal anti-inflammatory agents, for example fluocinolone or triamcinolone.

A topical formulation may contain 1-10% w/w of the oxadiazole derivative of the invention. A preferred pharmaceutical composition of the invention is one suitable for oral administration in unit dosage form, for example a tablet or capsule which contains between 100 mg. and 1000 mg. of the oxadiazole derivative, or one suitable for intravenous, subcutaneous or intramuscular injection, for example a sterile injectable containing between 1.0 and 20% w/w of the oxadiazole derivative.

The pharmaceutical composition of the invention will normally be administered to man for the treatment of peptic ulcers and other conditions caused or exacerbated by gastric acidity in the same general manner as that employed for cimetidine, due allowance being made in terms of dose levels for the potency of the guanidine derivative of the present invention relative to cimetidine. Thus each patient will receive an oral dose of between 100 mg. and 2000 mg., and preferably between 200 mg. and 500 mg., of oxadiazole derivative or an intravenous, subcutaneous or intramuscular dose of between 15 mg. and 500 mg., and preferably between 50 mg. and 300 mg., of the oxadiazole derivative, the composition being administered 2 to 4 times per day. The rectal dose will be approximately the same as the oral dose. The composition may be administered less frequently when it contains an amount of oxadiazole derivative which is a multiple of the amount which is effective when given 2-4 times per day.

Any of the well-known suitable pharmaceutical carriers can be used to prepare acceptable dosage forms so as to provide an effective amount or therapeutically effective amount of the compound to be administered.

| Tablet Containing 100 mg. of 3-[2-(2-cyano-3-methylguanidino) ethylthiomethyl]-5-guanidino-1, 2,4-oxadiazole | 1000 Tablets (Grams) |
|---|---|
| 3-[2-(2-cyano-3-methylguanidino) ethylthiomethyl]-5-guanidino-1,2, 4-oxadiazole | 100 |
| Starch | 102 |
| Powdered Lactose | 102 |
| Talc | 26 |
| Weight of Granulation | 330 |

Combine all ingredients, mix and then compress into slugs. The slugs should then be ground to form granules that will pass through a 14 to 16 mesh screen. The granules may then be recompressed into tablets using a suitable compression mold to form tablets, each weighing 280 mg.

| Capsule Containing 100 mg. of 3-[2-(2-cyano-3-methylguanidino) ethylthimethyl]-5-guanidino-1,2, 4-oxadiazole | |
|---|---|
| 3-[2-(2-cyano-3-methylguanidino) ethylthiomethyl]-5-guanidino-1,2, 4-oxadiazole | 100 mg. |
| Powdered Lactose | 200 mg. |
| D.T.D. Capsules No. 1000 | |

Mix the ingredients so as to evenly distribute the active ingredient throughout the lactose. Pack the powder into a No. 1 empty gelatin capsule.

The invention is illustrated, but not limited, by the following examples in which the temperatures are in degrees Centigrade:

EXAMPLE 1

Crude 3-[(2-aminoethyl)thiomethyl]-5-guanidino-1,2,4-oxadiazole and dimethyl (cyanoimido)dithiocarbonate (2.37 g.) were stirred in ethanol (150 ml.) for 18 hours at 20° C. The precipitated solid was filtered off, washed with petroleum ether (b.p. 40°-60°) and dried to give 3-[2-(3-cyano-2-methylisothioureido)ethylthiomethyl]-5-guanidino-1,2,4-oxodiazole, m.p. 197°-199°.

The crude 3-[(2-aminoethyl)thiomethyl]-5-guanidino-1,2,4-oxadiazole used as starting material may be prepared as follows:

A mixture of chloroacetamidoxime (27.1 g.), cyanoguanidine (21 g.), 12 N-hydrochloric acid (27 ml.) and ethanol (150 ml.) was heated under reflux for 20 hours, cooled and filtered. The filtrate was evaporated in vacuo to a gum which was extracted with hot ethyl acetate (5×100 ml.). The ethyl acetate extracts were evaporated to a mushy solid which was chromatographed on a silica column eluted with ethyl acetate. The major product, 3-chloromethyl-5-guanidino-1,2,4-oxadiazole, had an $R_F$ value of 0.55 on Merck 60 F-254 plates developed with ethyl acetate. This material was sufficiently pure for the next stage but a rechromatographed sample had a m.p. of 165°-168°.

Sodium methoxide (2.83 g.) was dissolved in dry ethanol (60 ml.) under argon and cooled to 0°. A solution of 2-aminoethanethiol hydrochloride (2.98 g.) in dry ethanol (30 ml.) was added and the mixture was stirred at 0° for 2 hours. A solution of 3-chloromethyl-5-guanidino-1,2,4-oxadiazole (2.3 g.) in dry ethanol (30 ml.) was added and stirring was continued for 1 hour at 0°. The temperature was then allowed to rise to 20° and stirring was continued for 18 hours. The mixture was filtered and the filtrate was evaporated to a yellow oil which was crude 3-[(2-aminoethyl)thiomethyl]-5-guanidino-1,2,4-oxadiazole. The product had an $R_F$ value of 0.4 on a Merck 60 F-254 plate developed with toluene/ethanol/ethyl acetate/0.880 ammonia in the ratio of 60:40:20:10 v/v/v/v.

EXAMPLE 2

To a solution of 3-[2-(3-cyano-2-methyl-isothioureido)ethylthiomethyl]-5-guanidino-1,2,4-oxadiazole (0.7 g.) in ethanol (20 ml.) was added a 33% w/v solution of methylamine in ethanol (30 ml.) The solution was kept for 18 hours at 20°, evaporated in vacuo and the residue finally dried at 30°/0.05 mm. to give 3-[2-(2-cyano-3-methylguanidino)ethylthiomethyl]-5-guanidino-1,2,4-oxadiazole as a white solid, m.p. 185°-188°.

EXAMPLE 3

A mixture of 3-[2-(3-cyano-2-methylisothioureido)ethylthiomethyl]-5-guanidino-1,2,4-oxadiazole and a saturated solution of ammonia in ethanol (60 ml.) was heated in a sealed tube for 4 hours at 70°. After cooling volatile material was evaporated in vacuo and the residue was chromatographed on a silica column eluted with methanol/chloroform 1:4 v/v. The product, 3-[2-(2-cyanoguanidino)ethylthiomethyl]-5-guanidino-1,2,4-oxadiazole, had m.p. 192°-195°.

EXAMPLE 4

A mixture of crude 3-[(2-aminoethyl)thiomethyl]-5-guanidino-1,2,4-oxadiazole (0.43 g.) and methyl isothiocyanate (0.15 g.) in absolute alcohol (20 ml.) was heated under reflux for 1 hour. Volatile material was evaporated in vacuo and the residue was chromatographed on a silica column eluted with methanol/chloroform, 1:4 v/v. The product, 5-guanidino-3-[2-(3-methylthioureido)ethylthiomethyl]-1,2,4-oxadiazole crystallised with a mole of methanol of crystallisation. (Found: C, 33.7; H, 5.4; N, 28.9; S, 19.5. $C_9H_{19}N_7O_2S_2$ requires C, 33.6; H, 5.9; N, 30.5; S, 19.9%).

EXAMPLE 5

A mixture of crude 3-[(2-aminoethyl)thiomethyl]-5-guanidino-1,2,4-oxadiazole (1.3 g.) and 1,1-bis(methylthio)-2-nitroethylene (0.99 g.) was stirred at 20° in ethanol for 3 days. The solvent was evaporated in vacuo and the residue was chromatographed on a silica column eluted with methanol/chloroform, 1:4 v/v. The crude product, 1-(2-[(5-guanidino-1,2,4-oxadiazol-3-yl)methylthio]ethyl)-amino-1-methylthio-2-nitroethylene (0.4 g.) was stirred for 18 hours with a 33% w/v solution of methylamine in ethanol (60 ml.) at 20°. The solution was evaporated in vacuo to a gum which was chromatographed on Merck 60 F-254 preparative plates developed with methanol/ethyl acetate, 1:3 v/v. The product 1-(2-[(5-guanidino-1,2,4-oxadiazol-3-yl)methylthio]ethyl)amino-1-methylamino-2-nitroethylene, was characterised by its n.m.r. spectrum in $d_6$ dimethyl sulphoxide using tetramethylsilane as an internal standard (δ=0):-6.5 (1H, singlet), 3.7 (2H, singlet), 3.35 (2H, multiplet), 2.75 (5H, multiplet).

What we claim is:

1. An oxadiazole derivative of the following formula (VI):

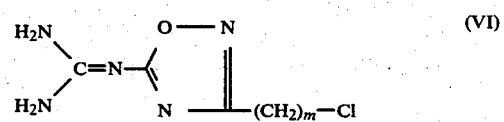

wherein
m is 1 to 4.

2. The oxadiazole derivative of claim 1, wherein said derivative is 3-chloromethyl-5-guanidino-1,2,4-oxadiazole.

* * * * *